(12) United States Patent
Shih et al.

(10) Patent No.: US 6,287,588 B1
(45) Date of Patent: Sep. 11, 2001

(54) AGENT DELIVERING SYSTEM COMPRISED OF MICROPARTICLE AND BIODEGRADABLE GEL WITH AN IMPROVED RELEASING PROFILE AND METHODS OF USE THEREOF

(75) Inventors: Chung Shih, Sandy; Gaylen M. Zentner, Salt Lake City, both of UT (US)

(73) Assignee: MacroMed, Inc., Sandy, UT (US)

( * ) Notice: Subject to any disclaimer, the term of this patent is extended or adjusted under 35 U.S.C. 154(b) by 0 days.

(21) Appl. No.: 09/559,507

(22) Filed: Apr. 27, 2000

Related U.S. Application Data

(60) Provisional application No. 60/131,562, filed on Apr. 29, 1999.

(51) Int. Cl.[7] ............................. A61F 2/00; A61F 9/14; A61F 9/50; A61F 47/30
(52) U.S. Cl. ........................ 424/426; 424/486; 424/489; 424/501; 514/772.3
(58) Field of Search .................................... 424/425, 423, 424/497, 501, 426, 486, 561, 424; 525/415

(56) References Cited

U.S. PATENT DOCUMENTS

| 4,652,441 | 3/1987 | Okada et al. |
|---|---|---|
| 5,476,663 | * 12/1995 | Okada et al. ........................ 424/423 |
| 5,643,605 | 7/1997 | Cleland et al. |
| 5,702,717 | * 12/1997 | Cha et al. ........................... 424/425 |
| 5,814,340 | 9/1998 | Labrie et al. |
| 6,117,949 | * 9/2000 | Rathi et al. ......................... 525/415 |

OTHER PUBLICATIONS

Jose Mario Barichello, et al.,Absorption of Insulin from Pluronic F–127 gels following subcutaneous administration in rats, *International Journal of Pharmaceutics*, 184 (1999) 189–198.

\* cited by examiner

*Primary Examiner*—Thurman K. Page
*Assistant Examiner*—Blessing Fubara
(74) *Attorney, Agent, or Firm*—Thorpe North & Western LLP

(57) ABSTRACT

A composition and method for releasing a bio-active agent or a drug within a biological environment in a controlled manner is disclosed. The composition is a dual phase polymeric agent-delivery composition comprising a continuous biocompatible gel phase, a discontinuous particulate phase comprising defined microparticles and an agent to be delivered. A microparticle containing a bio-active agent is releasably entrained within a biocompatible polymeric gel matrix. The bio-active agent release may be contained in the microparticle phase alone or in both the microparticles and the gel matrix. The release of the agent is prolonged over a period of time, and the delivery may be modulated and/or controlled. In addition, a second agent may be loaded in some of the microparticles and/or the gel matrix.

39 Claims, 1 Drawing Sheet

Figure 1:
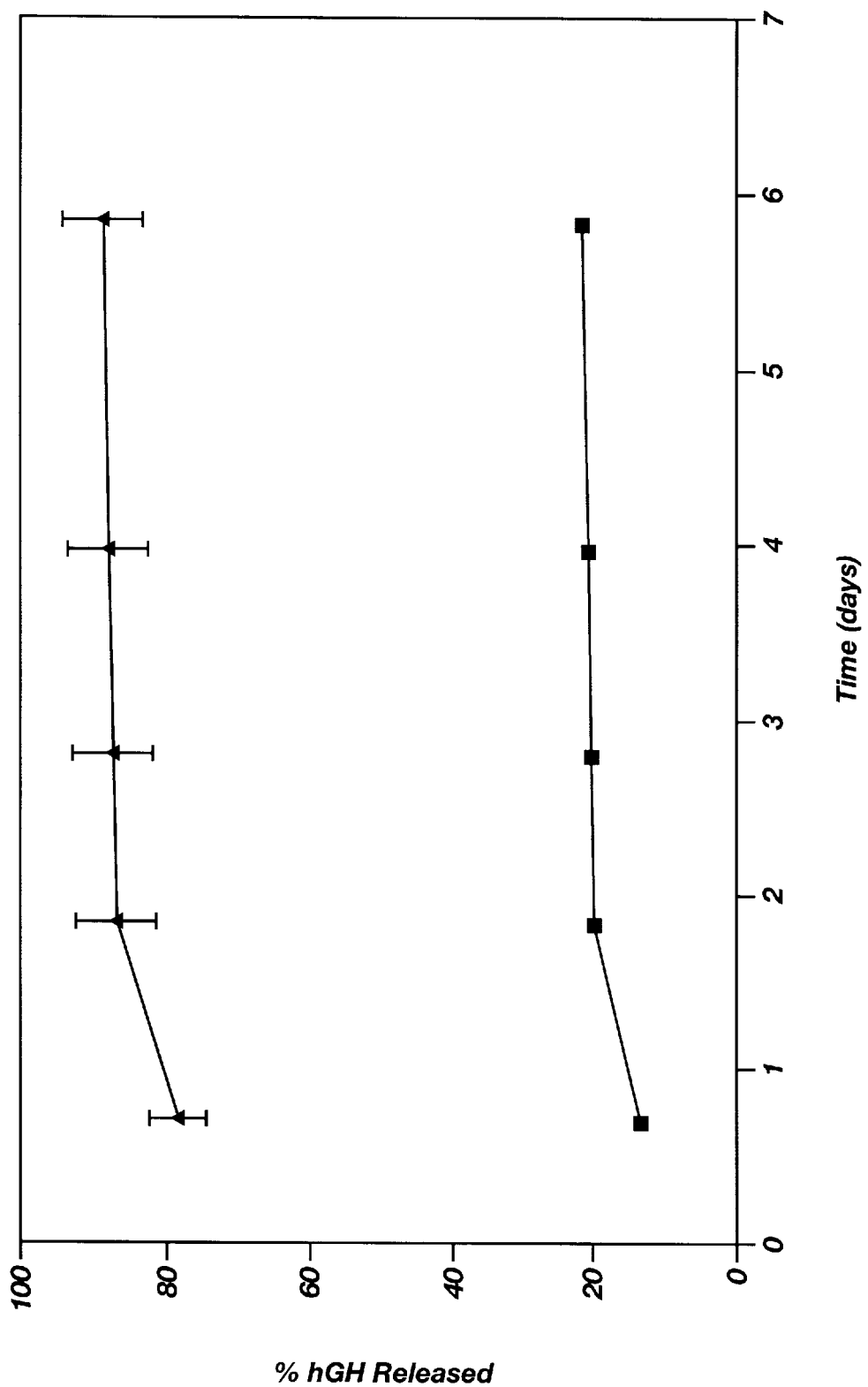

AGENT DELIVERING SYSTEM COMPRISED OF MICROPARTICLE AND BIODEGRADABLE GEL WITH AN IMPROVED RELEASING PROFILE AND METHODS OF USE THEREOF

RELATED APPLICATIONS AND PRIORITY CLAIM

This application claims the benefit of U.S. Provisional Application No. 60/131,562 filed Apr. 29, 1999.

FIELD OF THE INVENTION

The present invention is drawn toward a bioactive agent delivering system that allows for the prolonged and controlled release of a bioactive agent within an in vitro or in vivo environment. More specifically, the present invention comprises a biodegradable gel matrix and a microparticle system wherein the microparticle is embedded in the biodegradable gel matrix, from which the bioactive agent is released in a controlled manner. The bioactive agents may be located within the microparticle only, or within both the microparticle and the gel matrix.

BACKGROUND OF THE INVENTION

Many biologically active macro-molecules such as peptides/proteins and DNA, effective for gene therapy and a variety of therapeutic applications, have become commercially available through advances in recombinant DNA and other technologies. However, these molecules are limited to parenteral administration due to their susceptibility to degradation in the gastrointestinal tract. Treatment for chronic illnesses or indications may require multiple injections per day over many days, or months. Patient compliance is usually poor. Therefore, it would be highly desirable to develop a system for the delivery of bioactive agents or drugs, in particular, polypeptide or protein drugs, at a controlled rate over a sustained period of time without the above mentioned problems. This system would help to optimize the therapeutic efficacy, minimize the side effects, and thereby improve patient compliance.

Attempts to maintain a steady level of medication using biodegradable polymers have recently attracted considerable attention. These polymers are biodegradable and do not require retrieval after the medication is exhausted. Therefore, they can be fabricated into microspheres, microcapsules or nanospheres with the drug encapsulated in them. Various micro-encapsulation techniques incorporating a bioactive agent into a microparticle carrier are taught in the art, e.g. See U.S. Pat. Nos. 4,652,441; 5,100,669; 4,438,253 and 5,665,428.

However, burst release of the drug is often observed immediately after administration of the microparticle delivering systems. Release of the agent from a microparticle delivery system comprises an initial burst release from the surface of the device. Much higher than normal therapeutic levels of medication in the blood resulting from the burst effect of a microparticle system can cause side effects such as nausea, vomiting, delirium and, sometimes, death. Similar situations can occur when the polymer matrix is catastrophically eroded. Moreover, microparticle dosage forms are not retrievable should an adverse effect occur.

Therefore, it would be desirable to provide a bio-active agent delivery system that reduces "burst release" problem by incorporating the microparticle in a biocompatible, environmentally sensitive polymeric gel matrix. As such, the polymer gel would act as a secondary release barrier for the bio-active agent, reducing the effect of burst release. The microparticle-polymer gel bio-agent delivery system of the present invention provides better control of bio-active agent delivery than either the microparticles or the polymeric gel alone. In addition, since the microparticles are entrapped and localized, retrieval of the microparticel-gel system, if needed, is relatively easy.

OBJECTS AND SUMMARY OF THE PRESENT INVENTION

It is an object of the present invention to provide a dosage form that comprises a drug containing microparticle delivery system, which is suspended in a gelling solution. Upon administration within the body of a human or other warm-blooded animal and the gel sets, forming a depot and entrapping the drug-containing microparticles.

Another object of the present invention is to provide a controlled drug delivery system for the parenteral administration of hydrophilic and hydrophobic drugs, protein and peptide drugs, and oligo-nucleotides over an extended period.

Yet another object of this invention is to provide a drug delivery system that reduces the "burst" effect associated with microparticle delivery systems, improves the bioavailability and duration of action.

It is a further object of the present invention to provide a dosage form that can suspend the microparticles effectively and prevent plugging of hypodermic needles during administration.

Another object of the present invention is to provide a dosage form that localizes the microparticles in a gel depot that is easy to identify and retrieve, should surgical removal become necessary or prescribed.

It is another object of the present invention to provide a bio-active agent delivery system that localizes and protects the bio-active agent containing microparticles from enzyme degradation.

It is still another object of the present invention to provide a bio-active agent delivery system that enables the practioner to modulate release of the bio-active agent into the biological environment.

A further object of this invention is to provide a drug delivery system for the parenteral administration of hydrophilic and hydrophobic drugs, peptide and protein drugs, hormones, genes, oligonucleotides and anti-cancer agents.

These and other objects may be accomplished through a bio-active agent delivery system that combines two bio-active agent delivery technologies, namely, microparticle delivery and polymeric gel delivery. The agent delivery system of the present invention comprises a gel matrix and a microparticle system wherein the microparticle system is embedded in the gel matrix. One or more agents to be delivered may be located in the microparticle alone or both in the microparticle and the gel matrix. The microparticle-gel delivery system of the present invention can release the agent over a prolonged period of time, at a relatively constant rate. The release profile of the system can be modified by altering the microparticle and/or the gel composition. The gel solution is surface active and slightly more viscous than normal saline. Therefore, it can be a wetting agent and, at the same time, an excellent suspending agent for microparticles. This suspension can be injected smoothly without clogging using a relatively small-gauge needle. After injection, the gel sets and localizes the microparticle suspended in it. The agent encapsulated in the microparticle must be released from the microparticle before traveling through the gel matrix and entering the biological system. Therefore, the immediate release, or the burst, associated with microparticle delivery systems can be reduced and modulated. Since the release rates of the agent from these two systems can be quite different, embedding microparticles in the gel phase offers additional modulation and economical use of the agent. The benefits include higher bioavailability and longer duration of action than either system when used alone. Moreover, the combined system can improve the safety of microparticle dosage form. Since the microparticles are localized by the gel, they can be surgically retrieved, should one decide to terminate the medication delivery for any reason.

Artificial or natural microparticles including microcapsules, microspheres, and nanospheres contain the bio-active agent to be delivered to the body. Any bio-active agent having the ability to be contained and released by these microparticles may be used. The microparticles are then incorporated into a biocompatible polymeric gel that is capable of releasing the microparticles and/or bioactive material within the biological environment, in a controlled manner.

Additional objects and advantages of this invention will become apparent from the following summary and detailed description of the various embodiments making up this invention.

BRIEF DESCRIPTION OF DRAWINGS

FIG. 1. Effect of a reverse thermal gelation (RTG) system on the dissolution of human growth hormone (hGH) from Zn-hGH/PLG microspheres (100 mM HEPES, pH 7.4 at 37° C.). Samples with RTG (■) and without RTG (▲).

DETAILED DESCRIPTION OF THE INVENTION

Before the present invention comprising a biocompatible polymeric gel containing microparticles which release a desired bio-active agent into a biological environment, polymeric gel and/or both is disclosed and described, it is to be understood that this invention is not limited to the particular process steps and materials disclosed herein as such process steps and materials may vary to some degree. It is also to be understood that the terminology used herein is for the purpose of describing particular embodiments only and is not intended to be limiting as the scope of the present invention will be limited only by the appended claims and equivalents thereof.

As used herein the following terms shall have the assigned meanings:

Singular forms of "a," "an," and "the" include plural referents unless the content clearly dictates otherwise.

"Biocompatible" shall mean any substance that is suitable for uses in an warm-blooded animal or a human body.

"Biodegradable" means that the polymer gel and microparticle can break down or degrade within the body to non-toxic components after or while a bioactive agent has been or is being released.

"Parenteral" shall mean intramuscular, intraperitoneal, intra-abdominal, subcutaneous, and, to the extent feasible, intravenous and intraarterial.

"Bioactive agent", "bio-active agent" or "agent" shall mean any drug, organic compound, substance, nutrient or biologically beneficial agent including proteins, peptides (including polypeptides and oligopeptides) hormones, vaccines, oligonucleotides, nucleic acids, steroids, antibiotics, antibodies, live cells, tissue derived compositions and other pharmaceutically active agents. Suitable drugs are described in such well-known literature references as the Merck Index, the Physicians Desk Reference, and The Pharmacological Basis of Therapeutics. A brief listing of specific agents is provided for illustration purposes only, and shall not be deemed as limiting: anti-cancer agents such as mitomycin, bleomycin, BCNU, carboplatin, doxorubicin, daunorubicin, methotrexate, paclitaxel, taxotere, actinomycin D and camptothecin; antipsychotics such as olanzapine and ziprasidone; antibacterials such as cefoxitin; anthelmintics such as ivermectin; antivirals such as acyclovir; immunosuppressants such as cyclosporin A (cyclic polypeptide-type agent), steroids, and prostaglandins.

"Peptide," "polypeptide," "oligopeptide" and "protein" shall be used interchangeably when referring to peptide or protein drugs and shall not be limited as to any particular molecular weight, peptide sequence or length, field of bioactivity or therapeutic use unless specifically stated.

"Biological environment" shall mean any environment, whether in vitro or in vivo, where biological activity may be controlled by bioactive agent release. Preferably, the biological environment refers to warm blooded animals including human beings.

"Microparticles" shall include any particle capable of containing a bio-active agent that is to be released within the body including specialized forms such as microcapsules, microspheres, and nanospheres, and the like, whether natural or artificial.

"Microcapsules," "Microspheres" and "Nanospheres" refer generally to any highly-engineered and processed microparticle used to contain and release a bio-active agent.

"Gel" means the semi-solid phase that spontaneously occurs as the condition for the gelation of the polymer or copolymer is met.

"Polymeric gel" shall mean any polymer, copolymer, block copolymer and the like that exhibits gelation properties for a period of time when administered within a biological environment, but may be a liquid under conditions not present in that environment.

"Thermosensitive polymeric gel" shall mean any polymeric gel that, depending on temperature, may exist in liquid state or a gel state.

The terms "gelation temperature"or "gel/sol temperature" means the temperature at which a solution transitions to become a gel.

"Reverse Thermal Gelation"(RTG) or "Reverse Thermal Gelation system"(RTG system) refers to biodegradable block copolymers having reverse thermal gelation properties, i.e. are solutions at lower temperatures and transition to the gel state when at or above the gelation temperature. A detailed description of RTG systems has been disclosed in copending U.S. patent application Ser. No. 09/396,589 filed on Sep. 15, 1999, which is fully incorporated by reference herein.

"RTG mixture" or "blend of RTG" refers to a RTG system comprising a blend of two or more types of triblockcopolymers that have different block polymer ratios, molecular weights, gelations temperatures and the like. The RTG mixture or blend can be made either by simply mixing two or more individual previously synthesized poly(ethylene glycol)s with lactide, glycolide, carprolactone, and the like, to form a new RTG system, or by reacting two or more block copolymers to synthesize the mixed RTG system. The RTG mixtures or blends prepared by the above physical mixing or chemically reacting processes may have the same or different gelation properties and gel qualities.

"Polymer solution," "aqueous solution" and the like, when used in reference to a biodegradable polymer or block copolymer contained in such solution, shall mean a water based solution having a gel forming block copolymer dissolved therein at a functional concentration, and maintained at a temperature above or below the gelation temperature such that gel formation does not occur.

"Biodegradable polyesters" refers to any biodegradable polyester, which is preferably synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxy hexanoic acid, γ-butyrolactone, γ-hydroxy butyric acid, δ-valerolactone, δ-hydroxy valeric acid, hydrooxybutyric acids, malic acid, and copolymers thereof.

"Reverse thermal gelation" is the phenomena whereby a solution of a block copolymer spontaneously increases in viscosity, and in many instances transforms into a semisolid gel, as the temperature of the solution is increased above the gelation temperature of the copolymer. For the purposes of the invention, the term "gel" includes both the semisolid gel state and the high viscosity state that exists when gelation conditions are met. When cooled below the gelation temperature, the gel spontaneously reverses to reform the lower viscosity solution. This cycling between the solution and the gel may be repeated because the sol/gel transition does not involve any change in the chemical composition of the polymer system. All interactions to create the gel are physical in nature and do not involve the formation or breaking of covalent bonds.

"Microparticle-agent delivery liquid", "microparticle-agent delivery liquid having reverse thermal gelation properties" or "microparticle-agent delivery liquid having stimuli responsive gelation environment" shall mean a polymer solution that contains a microparticle carrying an agent to be delivered, e.g. a drug (the agent per se can either be dissolved or colloidal) suitable for administration to a warm-blooded animal which forms a gelled microparticle/drug depot when the temperature is changed, depending upon the properties of the polymer, to above or below the gelation temperature of the block copolymer, or when other gelation conditions are met.

"Depot" means a gel formed from a microparticle-agent delivery liquid following its administration to a warm-blooded animal when the temperature has been changed, depending upon the properties of the polymer, to above or below the gelation temperature or when other gelation conditions are met.

With the above definitions in mind and without unduly narrowing limitations, the present invention is directed toward a composition and method of preparing a bioactive agent delivery system comprising a drug containing microparticle delivery system suspended in gelling solution. Upon administration, the composition gelates and forms a depot, trapping the microparticles along with the drug incorporated in them. Optionally, a second bio-active agent may be contained in the microparticle and/or gel matrix.

The microparticles of the present invention may be microcapsules, microspheres, or nanospheres, currently known in the art, so long as they are capable of being entrained intact within a polymer that is or becomes a gel once inside a biological environment.

The microparticles of the present invention comprise a polymer matrix with biological active agents dispersed or encapsulated within. These polymers can be non-biodegradable or biodegradable. Non-biodegradable but biocompatible polymers include silicone rubber, polyethylene, poly(methyl methacrylate) (PMMA), polystyrene (PST) ethylene-vinyl acetate copolymer (EVA), polyethylene-maleic anhydride copolymers, polyamides and others. Although these polymers may be effective, they remain in the body after exhaustion of the biologically active agent. When necessary, they must be surgically removed.

Conversely, when using biodegradable and/or absorbable polymers as the carrier, the carrier is gradually degraded or absorbed in the body simultaneously with or subsequent to the release of the biologically active agent. Therefore, it is preferred that a biodegradable block copolymer is used in the present invention. Suitable biodegradable polymers for sustained release include biodegradable polyesters such as polylactides, poly(D,L-lactide-co-glycolide)s, polyglycolides, poly(lactic acid)s, poly(glycolic acid)s, poly (D,L-lactic acid-co-glycolic acid)s, poly-ε-caprolactone), poly(hydroxybutyric acid), and poly(amino acid)s, polyorthoesters, polyetheresters, polyphosphazines, polyanhydrides, polyesteramides, poly(alkyl cyanoacrylate) s, and blends and copolymers thereof. In a more preferred embodiment, the polymer is a biodegradable polyester or polyester copolymer. In a most preferred embodiment, the polymer is poly(D,L-lactide-co-glycolide) with molecular weight between 5,000 to 70,000 Daltons with a lactide-to-glycolide ratio of 1:1 to 1:0. The polymer end groups can be capped or uncapped with low molecular weight organic radicals.

Many microencapsulation techniques used to incorporate a bio-active agent into a microparticle carrier are taught in the art (U.S. Pat. Nos. 4,652,441, 5,100,669, 4,438,253, and 5,665,428). Commonly employed methods include: (a) phase separation and subsequent organic solvent evaporation (include O/W emulsion, W/O emulsions, O/O' emulsions and W/O/W emulsions), (b) coacervation, (c) melt dispersion; (d) spray drying, (e) spray congealing, (f) air suspension coating; and (h) pan coating.

The use of temperature sensitive biocompatible polymers as the gel matrix is a preferred embodiment of the present invention. For example, a block copolymer having thermal gelation properties wherein the polymer is a gel at physiological temperatures (approx.37° C.) and is a liquid above or below physiological temperatures would be functional. In the case of a gel having reverse thermal-gelation properties, the block copolymer would be a liquid at temperatures below the gelation temperature and would form a gel at above the gelation temperature. Conversely, a block copolymer having conventional thermal-gelation properties would be a liquid above the gelation temperature and a gel at or below the gelation temperature.

Biocompatible polymers having reverse gelation properties are most preferred for the present invention. For example, when a biocompatible block copolymer having reverse thermal-gelation properties is employed, microparticles containing bioactive agents could be loaded in the block copolymer at below physiological temperatures such as room temperature. Because such block copolymers are soluble in water when cooled, the microparticles may be easily loaded within the solution. Furthermore, when administered, the block copolymer solution, once in the gel state, is able to retain the microparticles and the bioactive agent to be released. In order to enter the biological environment, the agent encapsulated in the microparticle must overcome the barrier provided by the microparticle and the barrier provided by the gel matrix. If the block copolymer is in a gel state at the time of loading the microparticles, it would be much more difficult to incorporate the microparticles into the gel matrix. Additionally, if the block copolymer is a liquid at physiological temperature, the liquid copolymer would not be able to retain the microparticles. The bioactive agent maybe be released from the microparticles immediately. Polymers that exhibit conventional thermogelation characteristics would work similarly. The only difference would be that the microparticles would be loaded above physiological temperatures, i.e., when in the liquid state and would result in gel formation when cooled to body temperature.

It is important to keep in mind that biocompatible polymers exhibiting other properties may also be used. Thermosensitive polymers or gels are described above as merely a preferred embodiment. However, other environmentally sensitive polymers may be used such as those that respond to a changes in pH, ionic strength, solvent, pressure, stress, light intensity, electric field, magnetic field and/or specific chemical triggers such as glucose. The critical element is that the polymer be in a gel state for the period of time while within the body. Additionally, when considering what polymeric gels and/or microparticles to use, resistance to bioactive agent release is an important consideration. With some bioactive agent, where very prolonged and uniform release is desirable, gels and microparticles having a stronger and more uniform resistance (hence a more prolonged and uniform release of bioactive agent) should be selected. As such, polymeric gels and microparticles should be selected carefully based on how the bioactive agent is desired to be delivered.

A suitable polymeric gel for use with the present invention comprises ABA- or BAB-type block copolymers, where the A-blocks are relatively hydrophobic A polymer blocks comprising a biodegradable polyester, and the B-blocks are relatively hydrophilic B polymer blocks comprising polyethylene glycol (PEG). The A block is preferably a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-hydroxybutyric acid, δ-valerolactone, δ-hydroxyvaleric acid, hydroxybutyric acids, malic acid, and copolymers thereof, and the B block is PEG. In the most preferred embodiment, the A block is comprised of poly(D, L-lactide-co-glycolide) and the B block is PEG. Preferably, the triblcok copolymer has an average molecular weight between 300 and 20000 Daltons and contains about 10 to 83% by weight of A block polymer. More preferably, the triblcok copolymer has an average molecular weight between 500 and 5000 Daltons and contains about 51 to 83% by weight of A block polymer.

The polymeric gel is preferably biodegradable and exhibits water solubility at low temperatures and undergoes reversible thermal gelation at physiological mammalian body temperatures. Furthermore, these polymeric gels are biocompatible and capable of releasing the substance entrained within its matrix over time and in a controlled manner. As such, this polymeric gel, or others having desired properties, may be used to control release of various microparticles as described above. These biodegradable polymers are gradually degraded by enzymatic or non-enzymatic hydrolysis in aqueous or physiological environments. The degradation products are polyethylene glycol, lactic acid and glycolic acid. These compounds are relatively innocuous and can easily be excreted or absorbed by the biological system.

A distinct advantage of choosing a RTG system as the polymeric gel matrix in a preferred embodiment of the present invention lies in the ability of the RTG or RTG mixtures to wet and suspend the microparticles. The combination of hydrophobic A-block(s) and hydrophilic B-block (s) renders the block copolymer amphiphilic in nature. In that regard, it functions as a wetting agent. The viscosity of RTG is slightly higher than normal saline, thus it can also be seen as a thickening agent. The combination of these two properties makes RTG an excellent suspending agent for hydrophobic particles.

Another advantage to the delivery system of the invention lies in the ability of the drug/microparticle embedded polymeric gel to increase the chemical stability of many drug substances. As described earlier, the drug can be released into the biological environment via two pathways. The drug contained in the microparticle can be released into the polymeric gel matrix first, and then released from the gel matrix to the target. Alternatively, the microparticles containing the drug can be released first, and then the drug encapsulated in the microparticles may be released to the target. Various mechanisms for degradation of drugs/microparticles that lead to a drug's chemical instability have been observed to be inhibited when the drug is in the presence of the block copolymer. For example, paclitaxel and cyclosporin A are substantially stabilized in the aqueous polymer composition of the present invention relative to certain aqueous solutions of these same drugs in the presence of organic co-solvents. This stabilization effect on paclitaxel and cyclosporin A is but illustrative of the effect that would be achieved with many other drug substances. On the other hand, the present system significantly reduces the problem of the initial burst release effect of most microparticle drug delivery systems and the undesirable side effects caused by the overdose release.

In addition, the combination of microparticle and polymeric delivery systems also increases design flexibility of the drug delivery system to allow a fit to individual needs. Such drug delivery systems have modified or improved release profiles and individual delivery system through modulating the drug dissolution rate and gel matrix erosion rate.

The concentration at which the block copolymers are soluble at temperatures below the gelation temperature may be considered as the functional concentration. Generally speaking, block copolymer concentrations of as low as 3% and up to about 50% by weight can be used and still be functional. However, concentrations in the range of about 5 to 40% are preferred and concentrations in the range of about 10 to 30% by weight are most preferred. In order to obtain a viable gel phase transition with the copolymer, a certain minimum concentration, e.g. 3% by weight, is required. At the lower functional concentration ranges the phase transition may result in the formation of a weak gel. At higher concentrations, a strong gel network is formed.

The polymeric gel may be prepared as disclosed in copending application U.S. application Ser. No. 09/396,589 filed on Sep. 15, 1999 which are fully incorporated by reference herein. The microparticles carrying a bioactive agent may also be prepared according to methods known in the art. An aqueous solution of drug/microparticle below the gelation temperature forms a drug/microparticle delivery liquid where the drug may be either partially or completely dissolved. When the drug/microparticle is partially dissolved, or when the drug/microparticle is essentially insoluble, the drug-carrying microparticle exists in a colloidal state, such as a suspension or emulsion. This drug/ microparticle delivery liquid is then administered parenterally, topically, transdermally, transmucosally, inhaled, or inserted into a cavity such as by ocular, vaginal, transurethral, rectal, nasal, oral, buccal, pulmonary or aural administration to a patient, whereupon it will undergo reversible thermal gelation, or other stimuli responsive gelation.

The main mechanism of in vivo degradation of the polymers is by hydrolytic degradation in which enzymes may also play a role. Important factors influencing hydrolytic degradation include water permeability, chemical structure, molecular weight, morphology, glass transition temperature, additives, and other environmental factors such as pH, ionic strength, site of implantation, etc. The duration of sustained delivery can be adjusted from few days up to one year by a person of ordinary skill in the art through proper selection of polymer and fabrication method.

Release of the biologically active agent is usually triphasic. It comprises an initial burst or, immediate release of the agent present at or near the surface of the microparticle, a second phase during which the release rate is slow or sometime no bio-active agent is released, and a third phase during which most of the remainder of the biologically active agent is released as erosion proceeds. Any agent, as long as it is suitable for microencapsulation in a microparticle, as is known in the art, can utilize the delivery system described by the current invention.

Since the polymeric gel and/or microparticle of the delivery system of this invention are preferably biocompatible and biodegradable, there is minimal toxic effect and irritation to the host. The drug release profile can be controlled and improved by proper design and preparation of various gel forming polymers or copolymer blocks. The release profile of the polymeric gel may also be modified through preparation of a gel blend by selection of individual gel systems and ratios of individual gel systems in the blend. Drug release is also controllable through adjustment of the concentration of the gel blends in the drug delivery liquid. Although it is preferred in the present invention a RTG or a RTG mixture or blend is used, a gel blend of two or more non-RTG with desired gelation properties is also within the scope of the present invention.

An additional or a second agent can also be loaded into the microparticles and/or the polymeric gel matrix. The second agent can be a regulatory agent for the microparticle and/or the gel, or a second bio-active agent to be released into the biological environment in a same or different release rate.

The only limitation as to how much drug can be loaded into the microparticle and how much of such drug carrying microparticle can be loaded into the polymeric gel is one of functionality, namely, the drug/microparticle load may be increased until the microparticle structure, and/or the gelation properties of the polymer or copolymer are adversely affected to an unacceptable degree, or until the properties of the system are adversely affected to such a degree as to make administration of the system unacceptably difficult. Generally speaking, about 0.0001 to 30% by weight of a drug can be loaded into a microparticle with 0.001 to 20% being most common. The drug carrying microparticle will generally make up between 0.0001 to 30% by weight of the formulation with ranges of between about 0.001 to 20% being most common. These ranges of drug/microparticle loading are not limiting to the invention. Provided functionality is maintained, drug loadings outside of these ranges fall within the scope of the invention.

In certain situations the drug loaded microparticle/RTG polymer combinations may be administered in gel state instead of as a solution. Gelation may be the result of raising the temperature of drug laden microparticle/polymer solution to above the gelation temperature of the polymer prior to administration, or may be caused by raising the concentration of the gel forming polymer to the gel forming concentration, or may caused by additives which cause the gel forming polymer solution to gel, or when any other gelation conditions are met. In either event, the drug carrying microparticle/gel may be administered parenterally, topically, transdermally, transmucosally, inhaled or inserted into a cavity such as by ocular, vaginal, buccal, transurethral, rectal, nasal, oral, pulmonary or aural administration.

This invention is applicable to bio-active agents and drugs of all types including oligonucleotides, hormones, anticancer-agents, and it offers an unusually effective way to deliver polypeptides and proteins. Many labile peptide and protein drugs are amenable to formulation into the microparticle and/or the gel polymer or block copolymers and can benefit from the reverse thermal gelation process described herein. While not specifically limited to the following, examples of pharmaceutically useful polypeptides and proteins may be selected from the group consisting of erythropoietin, oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-$\alpha,\beta$, or $\gamma$, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), interleukin-12(IL-12),VEG-F, recombinant hepatitis B surface antigen(rHBsAg), renin, bradykinin, bacitracins, polymyxins, colistins, tyrocidine, gramicidins, cyclosporins and synthetic analogues, modifications and pharmacologically active fragments thereof, enzymes, cytokines, antibodies and vaccines.

The only limitation to the polypeptide or protein drug which may be utilized is one of functionality. In some instances, the functionality or physical stability of polypeptides and proteins can also be increased by the addition of various additives to aqueous solutions or suspensions of the polypeptide or protein drug. Additives, such as polyols (including sugars), amino acids, surfactants, polymers, other proteins and certain salts may be used. These additives can readily be incorporated into the microparticle/polymer gel system of the present invention, which will then undergo a gelation process.

Developments in protein engineering may provide for the possibility of increasing the inherent stability of peptides or proteins. While such resultant engineered or modified proteins may be regarded as new entities in regards to regulatory implications, that does not alter their suitability for use in the present invention. One of the typical examples of modification is PEGylation, where the stability of the polypeptide drugs can be significantly improved by covalently conjugating water-soluble polymers such as polyethylene glycol with the polypeptide. Another example is the modification of the amino acid sequence in terms of the identity or location of one or more amino acid residues by terminal and/or internal addition, deletion or substitution. Any improvement in stability enables a therapeutically effective polypeptide or protein to be continuously released over a prolonged period of time following a single administration of the drug delivery liquid to a patient.

In addition to peptide or protein based drugs and bioactive agents, any other agents needed to be delivered into an desired environment in controlled manner for a extended period, may be utilized in the present system; e.g, a food releasing system in a fish tank, or fertilizer/nutritional releasing system. Again, the only limitation is the compatibility between the agent and the microparticle and the polymeric gel.

The polymer gel may be pre-dissolved as a ready-to-use solution or may be in a powdered form that needs to be reconstituted with an aqueous vehicle. This solution is then mixed with microparticles before administration.

The present invention may be further illustrated by reference to the following examples.

EXAMPLE 1

This example illustrates the agent release profile (in vitro) of a microparticle-reverse thermal gelation(RTG) agent delivery system.

Zn-hGH, a representative human growth hormone drug, was incorporated into poly(D,L-lactide-co-glycolide) microspheres using the method described in U.S. Pat. No. 5,100,669, hereby fully incorporated by reference. Approximate 10 mg of the microspheres were weighed in a vial and to the vial was added to 100 μL of RTG solution (20% in 10 mM HEPES buffer, pH 7.0) to suspend the particles. The RTG gel was then set in a 37° C. oven and 1 mL of the dissolution medium (100 mM HEPES, pH 7.4 with 0.02% TWEEN-20, 37° C.) was added. The control was the identical microspheres suspended in dissolution medium without RTG. The vials were incubated in a 37° C. oven. Buffer was replaced periodically and the amount of hGH released was determined by HPLC. The result is shown in FIG. 1.

The data illustrated in FIG. 1 showed that a burst amounting to >80% of the loaded drug was observed when the RTG was absent as compared to <20% from those suspended in the RTG. Therefore, it is evident that the RTG-microparticle system of the present invention effectively reduced the initial burst effect of the microparticle delivery system.

EXAMPLE 2

This example illustrates the agent release profile (in vivo) of a microparticle-reverse thermal gelation(RTG) agent delivery system.

Zinc-hGH (12%) poly(D,L-lactide-co-glycolide) microspheres (160 mg) are suspended in 1.5 mL of a RTG(20% in 10 mM HEPES, pH 6.5). Three immuno-suppressed rats each is given 0.3-mL subcutaneous injections of the formulation in the dorsal lateral area. Rats in the control group are given the same dose of the microspheres but the vehicle is normal saline (with 3% low molecular weight carboxymethylcellulose as the suspending agent and 0.5% TWEEN 20). It is noticed that the RTG formulation can be injected smoothly using a 24-gauge needle (due to the excellent wetting and suspending ability of the RTG) while clogging of the needle often occurs in the control. Blood samples are collected periodically and the hGH concentrations in plasma are determined by radioimmunoassay (RIA). The plasma hGH profile of the rats given the RTG formulation shows a much smaller initial burst of hGH than those obtained from the control group. Burst is defined as the percent of hGH released (area-under-the-curve) in the first 24 hours. The elimination rate of the RTG group is significantly smaller than the control. Plasma hGH levels of the RTG group also maintain above the therapeutic level for longer than 4 weeks while those of the control group last ca. 2–3 weeks. Moreover, the bioavailability (area-under-the-curve) of the treatment group is ca.50% higher than that of the control.

EXAMPLE 3

This example illustrates the agent release profile (in vivo) of a microparticle-Pluronic® F127 agent delivery system. Pluronic® is a registered trademark of BASF for block copolymers of ethylene oxide and propylene oxide. Block copolymers of ethylene oxide and propylene oxide are not biodegradable.

Similar formulation described in Example 2 is used in this example except that the RTG is substituted with Pluronic® F127 (20% in 10 mM HEPES, pH 6.5). Rats in the controlled group are given same dose of the microspheres and the vehicle is normal saline (with 3% low molecular weight carboxymethylcellulose as the suspending agent and 0.5% TWEEN 20). Injections are smooth using 23-gauge needles. No plugging or clogging is experienced. Blood samples are collected periodically and hGH concentrations in plasma are determined by radioimmunoassay (RIA). Plasma hGH profile of the rats given microparticle-Pluronic® formulation shows a much smaller initial burst of hGH than those obtained from the control group.

EXAMPLE 4

This example illustrates the agent release profile (in vivo) of a microparticle-Tetronic®1307 agent delivery system. Teronic® is a registered trademark of BASF for amine based block copolymers.

Similar formulation described in Example 3 is used in this example except that the Pluronic® is substituted with Tetronic® 1307 (30% in 10 mM HEPES, pH 6.5) Rats in the controlled group are given same dose of the microspheres and the vehicle is normal saline (with 3% low molecular weight carboxymethylcellulose as the suspending agent and 0.5% TWEEN 20). Injections are smooth using 23-gauge needles. No plugging or clogging is experienced. Blood samples are collected periodically and hGH concentrations in plasma are determined by radioimmunoassay (RIA). Plasma hGH profile of the rats given microparticle-Tetronic® formulation shows a much smaller initial burst of hGH than those obtained from the control group.

EXAMPLE 5

This example illustrates the agent release profile (in vivo) of a microparticle-Carbomer 940 agent delivery system. Carbomer is also known as carbopol, or carboxylvinyl polymer.

Similar formulation described in Example 3 is used in this example except that the Pluronic® F127 is substituted with carbomer940(0.5% in 10 mM HEPES, pH 6.0). Rats in the controlled group are given same dose of the microspheres and the vehicle is normal saline (with 3% low molecular weight carboxymethylcellulose as the suspending agent and 0.5% TWEEN 20). Injections are smooth using 23-gauge needles. No plugging or clogging is experienced. Blood samples are collected periodically and hGH concentrations in plasma are determined by radioimmunoassay (RIA).

Plasma hGH profile of the rats given microparticle-Carbomer 940 formulation shows a relatively smaller initial burst of hGH than those obtained from the control group.

EXAMPLE 6

This example illustrate the preparation and the agent release profile (in vivo) of a non-biodegradable microshperes-RTG drug delivery system.

Ethylcellulose (1.5 g) is dissolved in 3 mL of acetonitrile in a container. Zn-hGH (150 mg) is then added to the container and the mixture is emulsified in 75 g of mineral oil containing 2% lecithin. The mixture is stirred (900 RPM) in a hood for >16 hrs using an overhead stirrer. Nitrogen (filtered through a 0.2 $\mu$filter) is swept over the head space of the container to remove solvents. The particles are allowed to settle down and the mineral oil is discarded. Hexane is then added to the container and the microspheres are collected by filtration. The microspheres are washed with hexane and the residual solvent is removed by vacuum. Particles passing a 120-mesh sieve are collected. 100 mg of the microspheres are suspended in 1 mL of RTG (20%) solution. Each rat (n=3) is given 300 $\mu$L of the suspension. Rats in control group (n=3) are given the same micropar-ticles suspended in normal saline (with 3% low molecular weight carboxymethylcellulose as the suspending agent and 0.5% TWEEN 20). Blood samples are taken periodically via tail vein. Plasma hGH levels are determine by RIA and show that the initial burst is substantially lower in rats given RTG formulation than those of the control.

EXAMPLE 7

This example illustrate the preparation and the agent release profile (in vivo) of a microshperes-RTG drug delivery system wherein the microparticle contains one drug and the gel matrix contains a second drug.

Erythropietin (Epogen® brand from Amgen) is incorporated into poly(D,L-lactide-co-glycolide) microspheres using the method described in U.S. Pat. No. 5,674,534, hereby incorporated by reference. Approximate 100 mg of the Epogen® microspheres (Epogen® loading is 10%) are suspended in 1 mL of RTG solution (20% in 10 mM HEPES buffer, pH 7.0) which contains 3 mg of granulocyte-colony stimulating factor(G-CSF). Each rat (n=6) is given 300 $\mu$L of the formulation. Rats in the controlled group (n=6) are given same dose of the Epogen® microspheres in normal saline (with 3% low molecular weight carboxymethylcellulose as the suspending agent and 0.5% TWEEN 20) containing the same amount of G-CSF of the test group. It is noticed that the RTG formulation can be injected smoothly using a 24-gauge needle (due to the excellent wetting and suspending ability of RTG) while clogging of the needle often occurs in the control. Blood samples are collected periodically and Epogen® and G-CSF concentrations in plasma are determined by radioimmunoassay (RIA). Plasma profile of the rats given RTG formulation shows a much smaller initial burst of Epogen® and G-CSF than those obtained from the control group. The elimination rate of these drugs in the microparticle-RTG formulation is significantly smaller than the control.

Three rats of each group are sacrificed 24 hrs after injection. It is found that all microparticles in the test group are trapped in RTG and can be easily identified and removed by a pair of tweezers while the microparticles in the control group are scattered and are very difficult to remove.

EXAMPLE 8

This example illustrate the preparation and the agent release profile (in vivo) of a microshperes-RTG drug delivery system wherein the drug is loaded both in the microparticles and the gel matrix.

100 mg Zn-hGH loaded microspheres (10% loading) prepared as described in Example 1 is suspended in 1 mL of RTG solution (20% in 10 mM HEPES buffer, pH 7.0) which contains 1 mg of hGH. Each rat (n=3) is given 300 $\mu$L of the microsphere-RTG formulation. Rats in the controlled group are given same dose of the microspheres in normal saline (with 3% low molecular weight carboxymethylcellulose as the suspending agent and 0.5% TWEEN 20) containing same amount of hGH. It is noticed that the RTG formulation can be injected smoothly using a 24-gauge needle (due to the excellent wetting and suspending ability of RTG) while clogging of the needle often occurs in the control. Blood samples are collected periodically and hGH concentration in plasma is determined by radioimmunoassay (RIA). Plasma profile of the rats given RTG formulation shows a lower and broader initial hGH peak than the control group. The elimination rate of the drug in the RTG group is also significantly smaller than the control.

EXAMPLE 9

This example illustrate the preparation and the agent release profile (in vivo) of a microparticle-RTG drug delivery system wherein some microparticles contains one drug, some microparticles contains a second drug.

Erythropoietin(Epogen®) is incorporated, at a loading of 10% (w/w), into poly(D,L-lactide-co-glycolide) microspheres using the method described in U.S. Pat. No. 5,674,534, hereby incorporated by reference. Separately, G-CSF (at 10% loading) is incorporated into poly(D,L-lactide-co-glycolide) microspheres using the same method. Both Epogen® and G-CSF containing microspheres (50 mg each) are suspended together in 1 mL of RTG solution (20% in 10 mM HEPES buffer, pH 7.0). Each rat (n=3) is given 300 $\mu$L of the formulation. Rats in the controlled group are given same dose of the microspheres in normal saline (with 3% low molecular weight carboxymethylcellulose as the suspending agent and 0.5% TWEEN 20) containing same amount of G-CSF or Epogen®. It is noticed that the RTG formulation can be injected smoothly using a 24-gauge needle (due to the excellent wetting and suspending ability of RTG) while clogging of the needle often occurs in the control. Blood samples are collected periodically and Epogen® and G-CSF concentrations in plasma are determined by radioimmunoassay (RIA). The initial burst of Epogen and G-CSF of the rats given RTG formulation is smaller than those obtained from the control group.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A dual phase polymeric agent-delivery composition comprising:
   (a) a continuous biocompatible gel phase,
   (b) a discontinuous particulate phase comprising defined microparticles; and
   (c) an agent to be delivered contained in both the continuous biocompatible gel phase and the discontinuous particulate phase.

2. The composition according to claim 1 wherein the biocompatible gel phase is biodegradable.

3. The composition according to claim 2 wherein said biodegradable gel comprises a hydrogel.

4. The composition according to claim 3 wherein said hydrogel is a stimuli responsive gel.

5. The composition according to claim 4 wherein said stimuli responsive gel is sensitive to stimuli selected from the group consisting of temperature, pH, ionic strength, solvent, pressure, stress, light intensity, electric field, magnetic field and gelating agents.

6. The composition according to claim 5 wherein said continuous gel phase is formed from block copolymers comprising an effective amount of biodegradable hydrophobic polyester A polymer blocks and polyethylene glycol B polymer blocks.

7. The composition according to claim 6 wherein the effective amount of biodegradable hydrophobic polyester A polymer blocks is 10–83% by weight of said block copolymer.

8. The composition according to claim 5 wherein said continuous gel phase is formed from a reverse thermal gelation (RTG) system comprising an effective amount of block copolymers comprising biodegradable hydrophobic polyester A polymer blocks and polyethylene glycol B polymer blocks.

9. The composition according to claim 8 wherein said RTG system is a mixture of two or more said block copolymers having different gelation properties.

10. The composition according to claim 9 wherein said RTG system comprises tri-block copolymers.

11. The composition according to claim 10 wherein said tri-block polymer comprises about 51 to 83% by weight of said biodegradable hydrophobic polyester, and about 17 to 49% by weight of polyethylene glycol(PEG).

12. The composition according to claim 8 wherein the biodegradable hydrophobic polyester is synthesized from monomers selected from the group consisting of D,L-lactide, D-lactide, L-lactide, D,L-lactic acid, D-lactic acid, L-lactic acid, glycolide, glycolic acid, $\epsilon$-caprolactone, $\epsilon$-hydroxy hexanoic acid, and copolymers thereof.

13. The composition according to claim 12 wherein the biodegradable hydrophobic polyester is synthesized from monomers selected from the group consisting of D,L-lactide, D-lactide, L-lactide, D,L-lactic acid, D-lactic acid, L-lactic acid, glycolide, glycolic acid, and copolymers thereof.

14. The composition according to claim 8 wherein the biodegradable hydrophobic polyester comprises between about 20 to 100 mole percent lactide and between about 0 to 80 mole percent glycolide.

15. The composition according to claim 10 wherein, in the triblock copolymer, each biodegradable block has an average molecular weight of between about 270 and 3000.

16. The composition according to claim 1 wherein said microparticle is in the form of a member selected from the group consisting of microcapsules, microspheres, and nanospheres.

17. The composition according to claim 16 wherein said microparticle is in the form of a member selected from the group consisting of microcapsules and microspheres.

18. The composition according to claim 1 wherein said microparticle is biodegradable.

19. The composition according to claim 18 wherein said agent is a bioactive agent, a drug, or any agent which can be loaded to the microparticle.

20. The composition according to claim 19 wherein said drug is a polypeptide or protein, oligonucleotide or gene, hormone, anti-cancer or anti-cell proliferation agent.

21. The composition according to claim 20 wherein said drug is a polypeptide or protein and is a member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, erythropoietin, somatostatin, glucagon, interleukin-2 (IL-2), interferon-$\alpha$, $\beta$, or $\gamma$, gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), HANP, glucagon-like peptide (GLP-1), interleukin-11 (IL-11), interleukin-12 (IL-12), VEG-F, recombinant hepatitis B surface antigen (rHBsAg), renin, bradykinin, bacitracins, polymyxins, colistins, tyrocidine, gramicidins, cyclosporins and synthetic analogues, modifications and pharmacologically active fragments thereof, enzymes, cytokines, antibodies and vaccines.

22. The composition according to claim 1 wherein the microparticle content of said composition is between about 0.0001 and 30% by weight.

23. The composition according to claim 1 wherein the drug content of said microparticle is between about 0.001 and 30% by weight.

24. The composition according to claim 21 wherein said polypeptide or protein is a member selected from the group consisting of erythropoietin, luteinizing hormone releasing hormone (LHRH), LHRH agonists, LHRH antagonists, growth hormones (human, porcine, bovine, etc.), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), glucagon-like peptide (GLP-1), interleukin-11 (IL-11), interleukin-12 (IL-12), VEG-F, recombinant hepatitis B surface antigen (rHBsAg), cyclosporins and synthetic analogues, modifications and pharmacologically active fragments thereof.

25. The composition according to claim 24 wherein said polypetide or protein is a human growth hormone, or synthetic analogue, modification and pharmacologically active fragment thereof.

26. The composition according to claim 19 wherein said drug is a member selected from the group consisting of testosterone, estradiol, progesterone, prostaglandins, leuprolide acetate, and synthetic analogues, modifications and pharmaceutically equivalents thereof.

27. The composition according to claim 19 wherein said drug is an anti-cancer agent selected from the group consisting of mitomycin, bleomycin, BCNU, carboplatin, doxorubicin, daunorubicin, methotrexate, paclitaxel, taxotere, actinomycin D, camptothecin, and synthetic analogues, modifications and pharmaceutically equivalents thereof.

28. The composition according to claim 1 further comprising a second agent.

29. The composition according to claim 28 wherein the second agent is a bioactive agent or a drug.

30. The composition according to claim 29 wherein some microparticles contain the first agent and other microparticles contain the second agent.

31. The composition according to claim 29 wherein the gel matrix contains both the first and the second agent.

32. The composition according to claim 28 wherein the second agent is an agent regulating the release profile of the microparticle.

33. A method for delivering an agent to a biological environment in a controlled manner for a prolonged period of time, comprising the steps of:

(1) providing a dual phase polymeric delivery composition according to claim 1, (2) maintaining said composition as a liquid; and (3) administering said composition as a liquid to the biological environment, with subsequent gel formation in the biological environment in response to a stimuli.

34. The method according to claim 33 wherein said administration is via parenteral, ocular, topical, inhalation, transdermal, vaginal, buccal, transmucosal, transurethral, rectal, nasal, oral, pulmonary or aural routes.

35. The method according to claim 33 wherein the biological environment is a warm blooded animal.

36. A method for delivering an agent to a biological environment in a controlled manner for a prolonged period of time, comprising the steps of:

(1) providing a dual phase polymeric delivery composition according to claim 1, (2) gelling said composition; and (3) administering said composition as a gel to the biological environment.

37. The method according to claim 36 wherein said administration is via parenteral, ocular, topical, inhalation, transdermal, vaginal, buccal, transmucosal, transurethral, rectal, nasal, oral, pulmonary or aural routes.

38. The method according to claim 37 wherein the biological environment is a warm blooded animal.

39. A method for enhancing the stability of a drug during the release from a microparticle delivery system process by providing a dual phase biodegradable polymeric delivery composition according to claim 1.

* * * * *